United States Patent [19]

Hatano et al.

[11] Patent Number: 5,496,787
[45] Date of Patent: Mar. 5, 1996

[54] PROCESS FOR PRODUCING A VANADIUM-PHOSPHORUS OXIDE CATALYST PRECURSOR

[75] Inventors: Masakatsu Hatano, Yokohama; Masayoshi Murayama, Yamato; Kenji Shima; Masumi Ito, both of Yokohama, all of Japan

[73] Assignee: Mitsubishi Chemical Corporation, Tokyo, Japan

[21] Appl. No.: 187,715

[22] Filed: Jan. 28, 1994

[30] Foreign Application Priority Data

Jan. 29, 1993 [JP] Japan ..................... 5-034348

[51] Int. Cl.⁶ .................................... B01J 23/22
[52] U.S. Cl. .................. 502/209; 502/208; 502/353; 423/305; 549/259; 549/262
[58] Field of Search ........................... 502/171, 208, 502/209, 353

[56] References Cited

U.S. PATENT DOCUMENTS

| | | | |
|---|---|---|---|
| 3,541,143 | 11/1970 | Nakano et al. | 502/209 |
| 3,579,573 | 5/1971 | Gilde et al. | 502/209 |
| 4,132,670 | 1/1979 | Katsumoto et al. . | |
| 4,333,853 | 6/1982 | Milberger et al. . | |
| 4,400,306 | 8/1983 | Dria et al. | 502/171 |
| 4,472,527 | 9/1984 | Otake et al. . | |
| 4,520,127 | 5/1985 | Otake et al. . | |
| 5,021,384 | 6/1991 | Hatano et al. . | |
| 5,128,299 | 7/1992 | Hatano et al. . | |

FOREIGN PATENT DOCUMENTS

| | | |
|---|---|---|
| 0098039 | 1/1984 | European Pat. Off. . |
| 0151912 | 8/1985 | European Pat. Off. . |
| 0466480 | 1/1992 | European Pat. Off. . |
| 0520972 | 12/1992 | European Pat. Off. . |

OTHER PUBLICATIONS

Applied Catalysts A: General, 95 (1993), L. M. Cornaglia, et al., "Chemistry of vanadium–phosphorus oxide catalyst preparation", 1993, pp. 117–130.

*Primary Examiner*—Anthony McFarlane
*Attorney, Agent, or Firm*—Oblon, Spivak, McClelland, Maier & Neustadt

[57] ABSTRACT

A process for producing a vanadium-phosphorus oxide-containing catalyst precursor, which comprises (a) introducing into an organic solvent a vanadium alkoxide as a pentavalent vanadium compound and a phosphorus compound in the presence of a reducing agent capable of reducing the pentavalent vanadium compound to a tetravalent state, (b) hydrolyzing at least a part of the vanadium alkoxide before or after the introduction of the phosphorus compound, and (c) heating the vanadium-containing liquid medium obtained in step (b), in the presence of the phosphorus compound to reduce at least a part of vanadium to a tetravalent state.

34 Claims, 6 Drawing Sheets

About 4 μm

About 4 μm

About 2 μm

About 3 μm

PROCESS FOR PRODUCING A VANADIUM-PHOSPHORUS OXIDE CATALYST PRECURSOR

The present invention relates to a process for producing a vanadium-phosphorus oxide catalyst precursor.

It has been well known since long ago that a vanadium-phosphorus oxide is a catalyst component effective for partial oxidation of a hydrocarbon or a carboxylic acid, for example, for the production of maleic anhydride by a gas phase catalytic oxidation reaction of a hydrocarbon having at least 4 carbon atoms.

In particular, in the case of the production of maleic anhydride from n-butane having low reactivity, a compound so-called divanadyl pyrophosphate $[(VO)_2P_2O_7]$ has been used as a catalytically active component (E. Bordes, P. Courtine, J. Catal., 57, 236–252, (1979)).

This catalyst is produced usually by a method which comprises calcining vanadyl hydrogen phosphate ½ hydrate ($VOHPO_4 \cdot ½H_2O$) as its precursor. It is known that by heating and calcining the precursor, it can be converted to divanadyl pyrophosphate while maintaining its structure.

Known as a method for producing such a vanadium-phosphorus catalyst precursor i.e. vanadyl hydrogen phosphate ½ hydrate, is a method which comprises dissolving vanadium pentoxide in an aqueous hydrochloric acid solution, adding phosphoric acid thereto, followed by concentration, or a method which comprises refluxing vanadium pentoxide in the presence of phosphoric acid in an organic solvent. With respect to these methods, many reports have been made, for example, Hodnett et al., Catalysis Review, 27, 373, (1985), Hutchings et al., Applied Catalysis, 72, 1, (1991), thus indicating substantial academic interest.

However, many catalyst precursors obtainable by the conventional methods have large particle sizes and are required to be pulverized to a size of micron order to be used as fluidized bed catalysts (see for example, Japanese Examined Patent Publication No. 63429/1991). Further, it has been reported that catalysts obtainable without such pulverization treatment are inferior in e.g. the catalytic properties or physical strength to the catalysts treated by such pulverization (see for example, Japanese Examined Patent Publication No. 57818/1991).

If it is possible to control the shape, the crystal size, etc. of the catalyst during the formation of the catalyst precursor, such a pulverization step will not be required, and it will be possible to simplify the process for producing the catalyst. Accordingly, the present inventors have conducted extensive studies for the purpose of developing a method which makes it possible to design the shape of the vanadium-phosphorus oxide catalyst precursor and as a result, have found it possible to adequately control the form, size, etc. of the catalyst precursor by appropriately regulating the process steps for formation of the catalyst precursor. The present invention has been accomplished on the basis of this discovery.

Thus, the present invention provides a process for producing a vanadium-phosphorus oxide-containing catalyst precursor, which comprises (a) introducing into an organic solvent a vanadium alkoxide as a pentavalent vanadium compound and a phosphorus compound in the presence of a reducing agent capable of reducing the pentavalent vanadium compound to a tetravalent state, (b) hydrolyzing at least a part of the vanadium alkoxide before or after the introduction of the phosphorus compound, and (c) heating the vanadium-containing liquid medium obtained in step (b), in the presence of the phosphorus compound to reduce at least a part of vanadium to a tetravalent state.

Now, the present invention will be described in detail.

The pentavalent vanadium compound to be used as a starting material for the catalyst precursor of the present invention is a vanadium alkoxide. This vanadium alkoxide is usually synthesized ① by dehydrative condensation of an alcohol with vanadium pentoxide, ② by a ligand exchange reaction of a vanadium alkoxide with an alcohol, ③ by a dehalogenation reaction of a vanadyl trihalide such as $VOCl_3$ with an alcohol. Preferred is the method ①. Most commonly, the vanadium alkoxide is obtained by dehydrative condensation of a $C_{1-5}$ alcohol with vanadium pentoxide. Specific vanadium alkoxides include, for example, vanadium methoxide, vanadium ethoxide, vanadium n-propoxide, vanadium n-butoxide and vanadium i-butoxide.

As the vanadium alkoxide, a synthesized product may usually be used as it is. Namely, after the dehydrative condensation of the alcohol with the vanadium compound as described above, the reaction product may be subjected directly to the production of the catalyst precursor of the present invention in the same reactor. In such a case, the vanadium compound as the starting material may not necessarily be completely converted to an alkoxide. However, it is usually preferred that at least 50%, preferably at least 70%, more preferably at least 80%, of the starting material vanadium compound is converted to an alkoxide.

The phosphorus compound to be used in the present invention may, for example, be a tetravalent phosphorus compound such as orthophosphoric acid, pyrophosphoric acid, methaphosphoric acid, phosphorus pentoxide, monoammonium phosphate, diammonium phosphate or triammonium phosphate. Among them, preferred is orthophosphoric acid. Such orthophosphoric acid may be commercially available 85% phosphoric acid, or a mixed phosphoric acid containing pyrophosphoric acid or methaphosphoric acid together with orthophosphoric acid, or it may be phosphoric anhydride.

With respect to the proportions of the starting material vanadium alkoxide and the phosphorus compound, the atomic ratio of phosphorus/vanadium is usually from 1.0 to 1.5, preferably from 1.05 to 1.3.

The organic solvent to be used in the present invention may suitably be selected among organic compounds such as alcohols, carboxylic acids, ethers and esters. It is preferred to use a reducing organic compound, since such an organic compound will serve not only as a solvent but also as a reducing agent in the reaction system. Such an organic compound may, for example, be one having a functional group susceptible to oxidation or one capable of forming a functional group susceptible to oxidation, during the heating or the reaction. Typically, a compound having an alcoholic hydroxyl group is preferred. Among such compounds, an aliphatic alcohol having from 3 to 6 carbon atoms is particularly preferred. Propanol, butanol, hexanol or 2-methyl-propanol may, for example, be mentioned.

Otherwise, a reducing agent such as hydrazine or oxalic acid may separately be added for the reduction in an organic solvent. Even when the organic solvent itself has a reducing power, an unsaturated alcohol such as benzyl alcohol, or other reducing agent having a stronger reducing power may further be added. In the present invention, there is a general tendency that as the reducing power in the reaction system increases, it is more readily possible to obtain a scaly catalyst precursor having a smaller particle size. As a method for forming a reaction system having such a strong reducing power, it is preferred to employ a method of using a mixture of an aliphatic alcohol having from 3 to 6 carbon atoms and benzyl alcohol, as the organic solvent. Further, in the present invention, the solvent may not necessarily be substantially anhydrous, since the process includes a step of hydrolyzing the vanadium alkoxide. The organic solvent is used usually from 1 to 30 parts by weight, preferably from 2 to 15 parts by weight, per part by weight of the total amount of the vanadium alkoxide and the phosphorus compound as starting materials.

Using the above described starting material compounds, the present invention is characterized in that a vanadium alkoxide as a pentavalent vanadium compound and a phosphorus compound are introduced into an organic solvent in the presence of a reducing agent which is capable of reducing the pentavalent vanadium compound to a tetravalent state, and at least a part of the vanadium alkoxide is hydrolyzed before or after the introduction of the phosphorus compound.

Firstly, an embodiment will be described in which at least a part of the vanadium alkoxide is hydrolyzed, followed by a reaction with the phosphorus compound.

The hydrolysis of the vanadium alkoxide is conducted within a temperature range of from room temperature to the refluxing temperature of the solution, usually from 0 to 150° C., preferably from 20° to 100° C., usually by an addition of water in an amount required for the hydrolysis to the organic solvent solution of the vanadium alkoxide. The amount of water to be added for the hydrolysis is usually from 0.5 to 20 mols, preferably from 1 to 5 mols, per mol of the vanadium alkoxide. The organic solvent for the vanadium alkoxide may be all the amount used for the reaction of the catalyst precursor or a part thereof. Otherwise, it is preferred to employ a method of adding a solvent having a strong reducing power after the hydrolysis.

Further, in the present invention, it is possible to control the shape of the finally obtainable catalyst precursor by adding an acid or a base at the time of the hydrolysis. Namely, when a base is added, a three dimensionally developed catalyst precursor having a large particle size is likely to be obtained. On the other hand, when an acid is added, a catalyst precursor having a small particle size is likely to be obtained. The pH during the hydrolysis may vary depending upon the desired shape of the catalyst precursor, but the pH is usually within a range of from 0 to 12, preferably from 1 to 10.

The above described hydrolytic reaction proceeds swiftly from the time when water is added to the vanadium alkoxide, and the reaction is considered to substantially complete in a relatively short period of time. However, after the addition of water, the reaction product may be left to stand for a while for aging. Such aging time is usually from 0.1 to 10 hours, preferably from 0.2 to 1 hour.

After the above hydrolysis, the phosphorus compound is added, and in some cases, an organic solvent or a reducing agent is further added. The resulting slurry-like solution is reacted to form a vanadium-phosphorus oxide catalyst precursor. In this case, the above slurry-like solution is usually mixed and then heated and refluxed usually at a temperature at a level of the boiling point of the organic solvent, for example, from 50° to 200° C. to reduce all or a part of vanadium to a tetravalent state, and at the same time, the phosphorus compound is reacted, to obtain crystalline oxide particles containing tetravalent vanadium and phosphorus. Here, it is also possible to employ a method wherein before the addition of the phosphorus compound, heating and refluxing are preliminarily conducted to carry out the reduction of vanadium to some extent, and then the phosphorus compound is added, and heating and refluxing are conducted again. The heating and refluxing time necessary for the formation of the catalyst precursor is usually from 0.5 to 20 hours, preferably from 2 to 10 hours.

The oxide particles obtainable from the above starting materials do not necessarily have good crystallinity, but at least partially contain vanadyl hydrogen phosphate ½ hydrate. The obtained particles can be taken out as a catalyst precursor by a common method for solid-liquid separation such as evaporation to dryness, spray drying, centrifugal separation or filtration.

Secondly, an embodiment will be described in which the phosphorus compound is added prior to the hydrolysis of the vanadium alkoxide, so that the hydrolysis of the vanadium alkoxide, the reduction of vanadium and the reaction with the phosphorus compound are conducted simultaneously.

In such a case, the vanadium alkoxide is added to an organic solvent solution containing the phosphorus compound, and the resulting slurry-like solution is mixed and heated and refluxed usually at a temperature at a level of the boiling point of the organic solvent, for example, from 50° to 200° C. to reduce all or a part of vanadium to a tetravalent state. At a suitable time during the above reaction, water in an amount necessary for the hydrolysis of the vanadium alkoxide, is added to the reaction solution, so that the phosphorus compound is reacted therewith, to obtain crystalline oxide particles containing tetravalent vanadium and phosphorus. The heating and refluxing time required for the formation of the catalyst precursor is usually from 0.5 to 20 hours, preferably from 2 to 10 hours. The timing for the addition of water is preferably during a period of from 0 to 2 hours from the initiation of refluxing. Further, the amount of water to be added for the hydrolysis is usually from 0.5 to 20 mols, preferably from 1 to 5 mols, per mol of the vanadium alkoxide.

The oxide particles obtained by the above method can be withdrawn in the form of a solid by a common method for solid-liquid separation in the same manner as in the above described first embodiment of the present invention.

Further, in the present invention, a compound containing other metal elements may be added as a co-catalyst component during the above described process for the formation of the catalyst precursor to effectively modify the catalyst. As the metal elements useful for this purpose, one or more metal elements selected from the group consisting of chromium, iron, nickel, cobalt, zinc, ruthenium and zirconium, may be mentioned. Nitrates, chlorides, sulfates or organic acid salts of these metal elements may be incorporated from the beginning of the reaction or after the addition of the phosphorus compound to effectively modify the catalyst. The amount of such metal elements to be added is usually from 0.001 to 0.30 mol, preferably from 0.02 to 0.10 mol, per mol of vanadium.

The vanadium-phosphorus oxide catalyst precursor obtained by the above described method, will usually be finally calcined at a temperature of from 300° to 700° C. for activation to convert at least a part of the precursor oxide to divanadyl pyrophosphate, so that it is useful as a catalyst. As an example of such calcination condition, heating in a nitrogen atmosphere or a atmosphere having nitrogen and air mixed at suitable proportions or in a reactive gas atmosphere, may be mentioned.

Further, the precursor of the oxide catalyst of the present invention may be mixed by itself with a binder component or a carrier component, followed by drying and heating for activation. Otherwise, the precursor may be preliminarily heated for activation, and then mixed with a binder component or a carrier component, followed by drying. Then, the product is molded as the case requires depending upon the type of the reactor to form an industrial catalyst.

Such a catalyst is useful for a partial oxidation reaction of a hydrocarbon or a carboxylic acid, particularly for the production of maleic anhydride by a gas phase oxidation of a hydrocarbon having at least 4 carbon atoms such as n-butane, 1-butene, 2-butene, 1,3-butadiene or benzene. Particularly economically advantageous as such a hydrocarbon starting material are n-butane and butene. These starting materials can readily be obtained by separation from a natural gas or by separation from a cracking product of naphtha. The oxidation reaction system may be a fluidized bed system or a fixed bed system. As the oxidizing agent, air or a molecular oxygen-containing gas may be employed. The hydrocarbon starting material is usually from 0.1 to 10 vol %, preferably from 1 to 5 vol%, and the oxygen concentration is usually from 10 to 30 vol%. The reaction temperature is usually from 300° to 550° C., preferably from 350° to 500° C. The reaction is conducted usually under atmospheric pressure or an elevated pressure of from 0.05 to 10 kg/cm$^2$G.

In the present invention, for the formation of the vanadium-phosphorus oxide catalyst precursor by the reaction of a pentavalent vanadium compound and a phosphorus compound in the presence of a reducing agent in an organic solvent, a vanadium alkoxide is used as the starting pentavalent vanadium compound. And the feature of the present invention resides in that the vanadium alkoxide is hydrolyzed, and then the hydrate gel product of vanadium pentoxide thereby formed is reacted with the phosphorus compound.

By the reaction of the hydrate gel product of vanadium pentoxide with the phosphorus compound, it is possible to readily control the size and the shape of the resulting catalyst precursor or the reactivity when formed into a catalyst by suitably selecting the reaction conditions, as compared with the conventional methods.

For example, when the vanadium alkoxide is hydrolyzed in the presence of an acid, a catalyst precursor having a small particle size is likely to obtain, and if the hydrolysis is conducted in the presence of a base, a catalyst precursor having a large particle size is likely to be obtained. Further, when the condition for reducing vanadium is increased, a catalyst precursor having a small particle size is likely to be obtained.

The reason why the size and shape of the catalyst precursor obtainable in the present invention can easily be controlled, is not clearly understood, but the following assumption may be made.

Heretofore, vanadium pentoxide is mainly employed as the starting pentavalent vanadium compound. Vanadium pentoxide usually has high crystallinity and is hardly reacted with a phosphorus compound such as phosphoric acid at room temperature and can be made to be reacted only when sufficiently heated. Thus, the reactivity is not so high. Accordingly, an influence of the reaction condition over the shape, etc. for the resulting catalyst precursor may not be substantial. On the other hand, the hydrate gel product of vanadium pentoxide formed by the hydrolysis of the vanadium alkoxide is considered to be non-crystalline in many cases, and as compared with crystalline vanadium pentoxide, the reactivity at its surface is high, whereby it is considered to be susceptible to an influence of the reaction conditions over the shape, etc. of the resulting catalyst precursor.

Now, embodiments of the present invention will be described in further detail with reference to Examples. However, it should be understood that the present invention is by no means restricted by such specific Examples.

The average particle size of the catalyst precursor in Table 1 was measured by a particle size distribution meter of a laser scattering type after dispersing the catalyst precursor in water, and it roughly corresponds to the value obtained by a scanning electron microscopic photograph.

EXAMPLE 1

Figure 1:
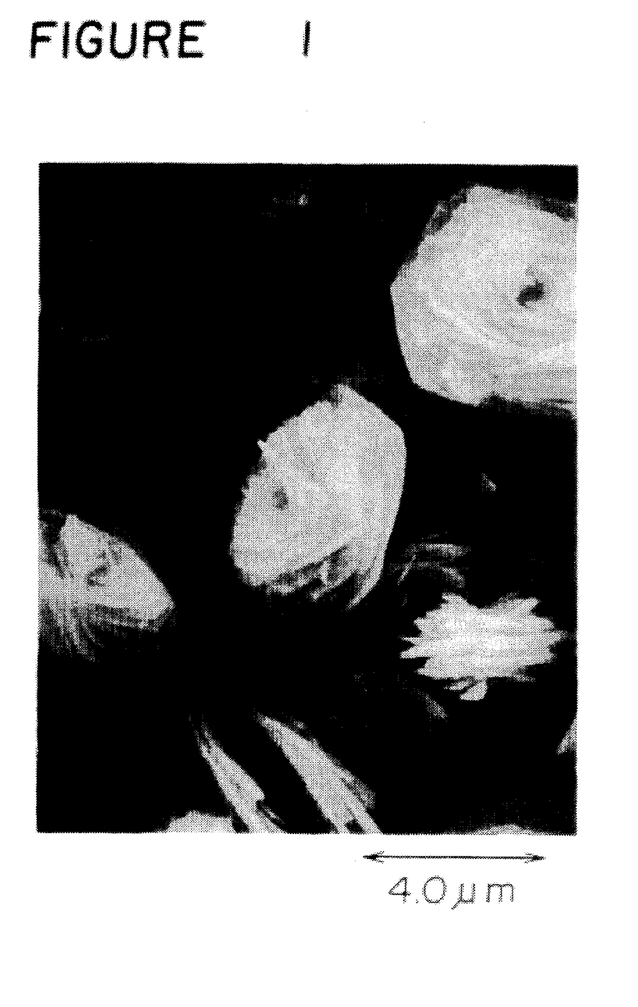
FIG. 1 is a photograph showing the particle structure of the catalyst precursor A obtained in Example 1 (6,000 magnifications).
Figure 2:
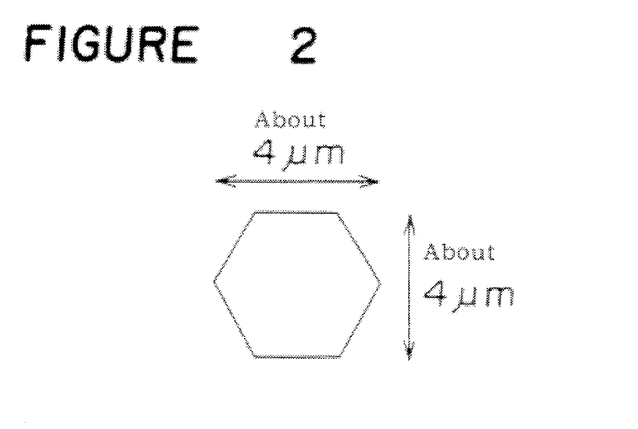
FIG. 2 is a diagrammatical view showing the shape of one crystal particle of the catalyst precursor A obtained in Example 1.

30 g of vanadium n-butoxide was charged into a 300 ml three necked flask, and 150 ml of isobutanol was added thereto as a solvent. An isobutanol solution having 3.48 g of water dissolved therein, was slowly dropwise added thereto, whereby the alkoxide was hydrolyzed to form a yellow precipitate. Then, 14.5 g of 85% phosphoric acid was added thereto, and the mixture was stirred and heated, and refluxing was continued to obtain a blue solid. After refluxing for 6 hours, the mixture was cooled and subjected to filtration to obtain a catalyst precursor A. The catalyst precursor A had a size and shape as shown in FIGS. 1 and 2.

EXAMPLE 2

Figure 3:
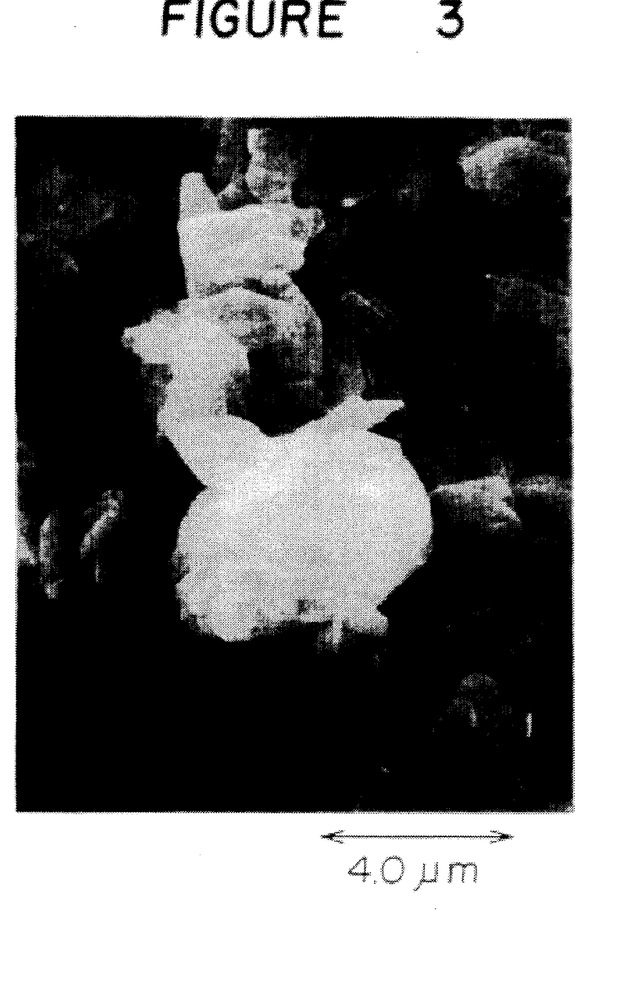
FIG. 3 is a photograph showing the particle structure of the catalyst precursor B obtained in Example 2 (6,000 magnifications).
Figure 4:
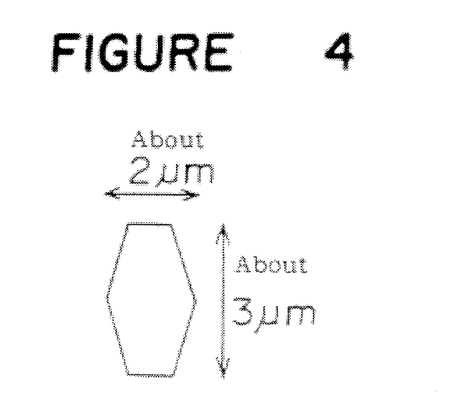
FIG. 4 is a diagrammatical view showing the shape of one crystal particle of the catalyst precursor B obtained in Example 2.

A catalyst precursor B was prepared in the same manner as in Example 1 except that 21.2 g of vanadium ethoxide was employed instead of vanadium n-butoxide. The catalyst precursor B had a size and shape as shown in FIGS. 3 and 4.

EXAMPLE 3

Figure 8:
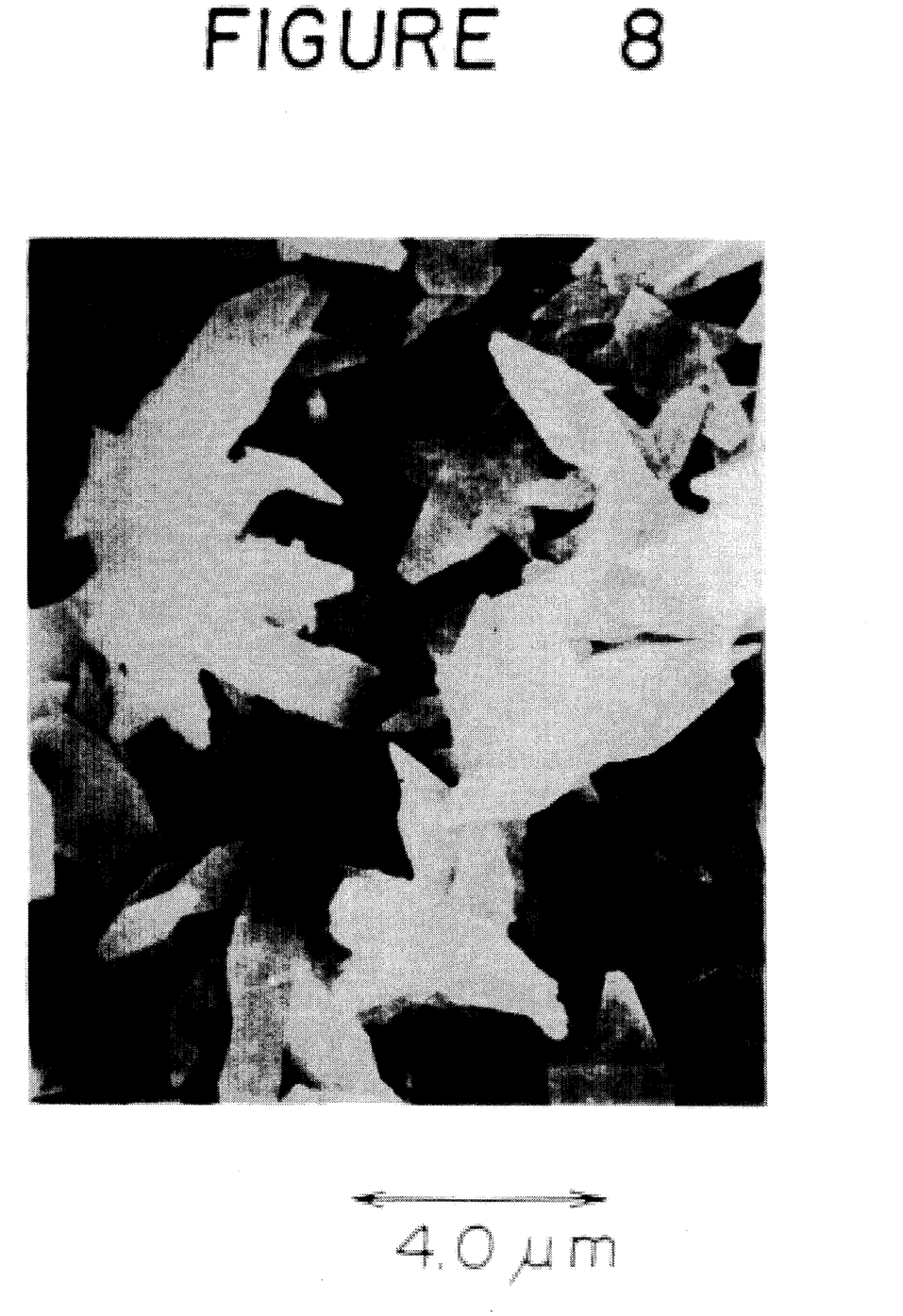
FIG. 8 is a photograph showing the particle structure of the catalyst precursor C obtained in Example 3 (6,000 magnifications).

60 ml of n-propanol and 60 ml of toluene were added to 18.2 g of vanadium pentoxide. The mixture was heated to 90° C., and formed water was azeotropically removed to obtain vanadium propoxide. Here, about 60% of vanadium pentoxide was converted to vanadium propoxide. To such the reaction solution, 70 ml of isobutanol was added, and 7.2 ml of water was further added for hydrolysis, whereby a gel-like precipitate formed. Then, 200 ml of butanol and 32.8 g of 100% phosphoric acid were added thereto. The temperature was raised with stirring, and refluxing was continued to obtain a blue solid. After conducting the refluxing for 10 hours, the mixture was cooled and subjected to filtration to obtain a catalyst precursor C. The catalyst precursor C had a size and shape as shown in FIG. 8.

COMPARATIVE EXAMPLE 1

Figure 5:
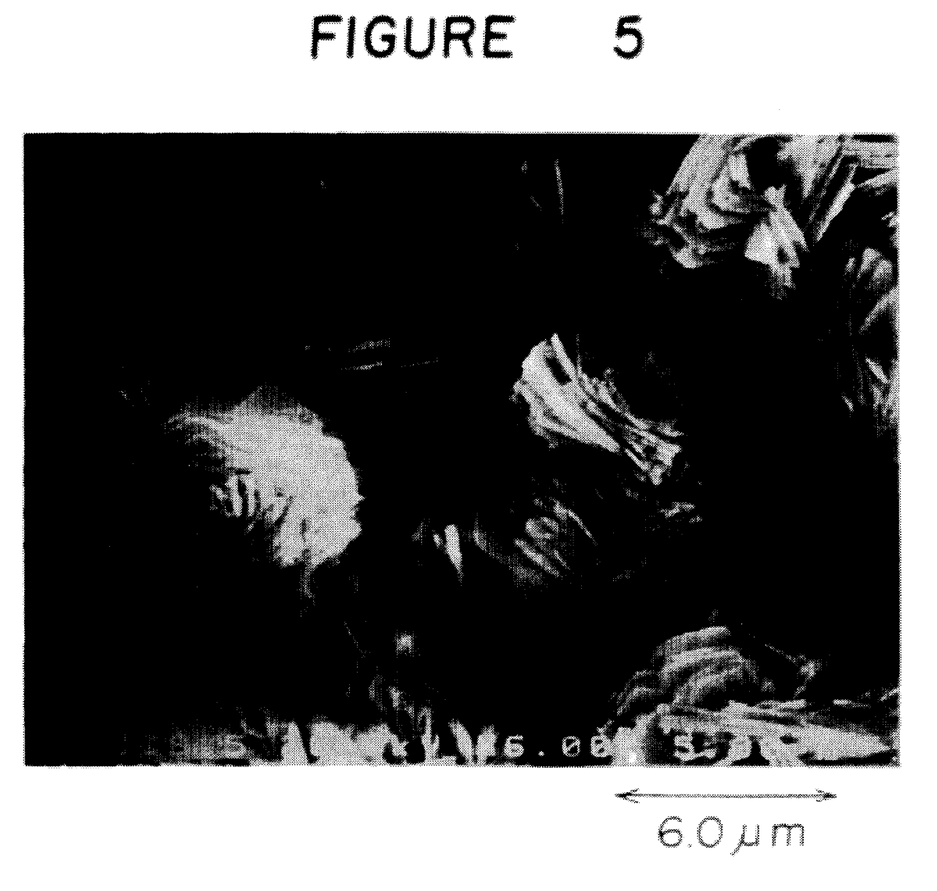
FIG. 5 is a photograph showing the particle structure of the catalyst precursor D obtained in Comparative Example 1 (6,000 magnifications).

18.2 g of vanadium pentoxide and 27.7 g of 85% phosphoric acid were added to 200 ml of isobutanol. The mixture was refluxed for 6 hours, and a white solid thereby obtained was separated by filtration to obtain a catalyst precursor D. The catalyst precursor D had a size and shape as shown in FIG. 5. As compared with the case where an alkoxide was used as the starting material, the particle size was large, and the shape itself was different.

EXAMPLE 4

Figure 6:
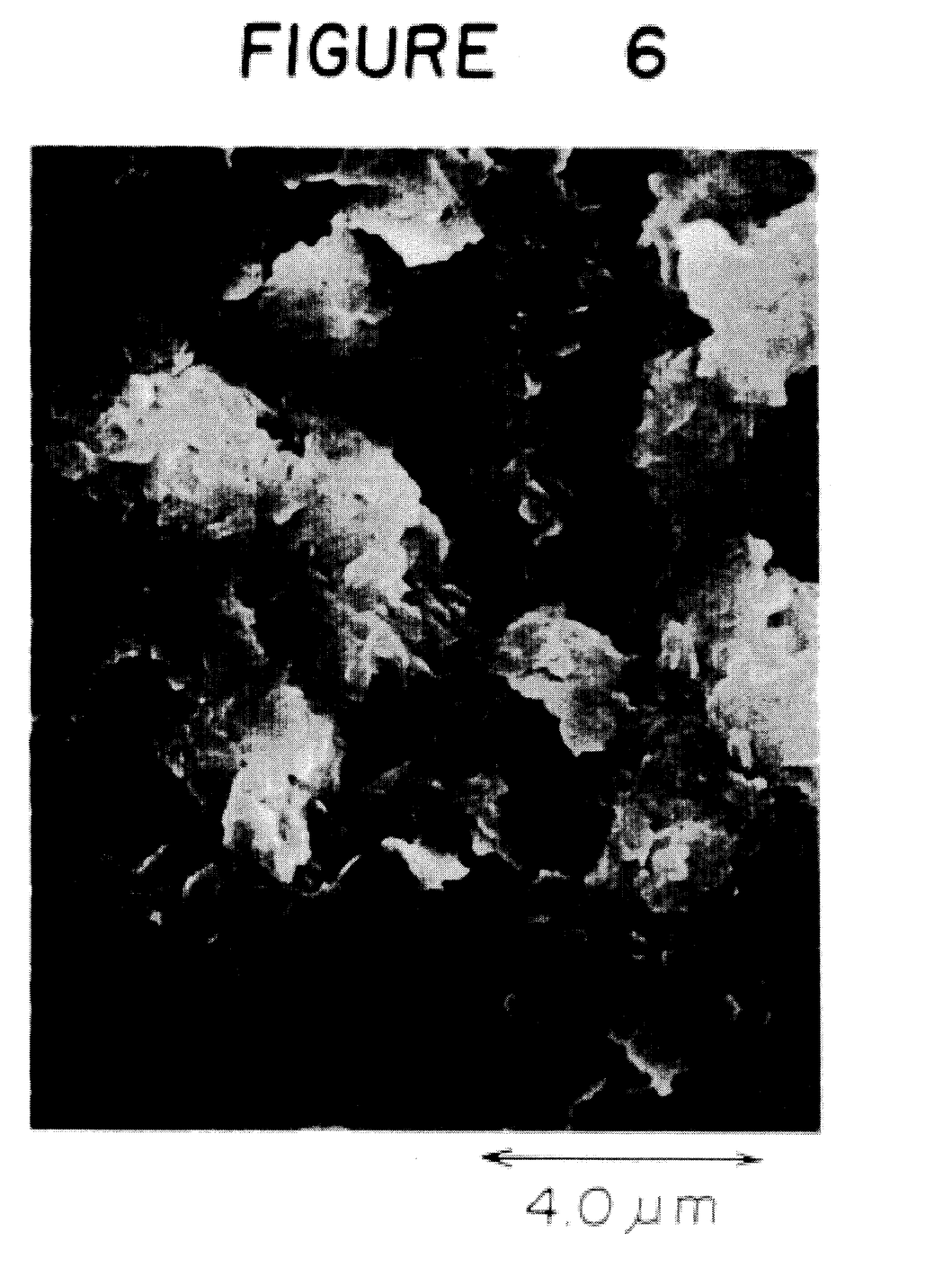
FIG. 6 is a photograph showing the particle structure of the catalyst precursor E obtained in Example 4 (6,000 magnifications).

A catalyst precursor E was prepared in the same manner as in Example 1 except that 100 ml of n-propanol was used as the solvent and 56.6 g of benzyl alcohol was added as a reducing agent. The catalyst precursor E had a size and shape as shown in FIG. 6.

EXAMPLE 5

30 g of vanadium tri-n-butoxide was charged into a 300 ml three necked flask, and 150 ml of isobutanol was added thereto as a solvent. The mixture was heated. When the temperature reached to the refluxing temperature, 14.5 g of 85% phosphoric acid and an isobutanol solution having 3.48 g of water dissolved therein were sequentially added thereto. Refluxing was continued to obtain a blue solid. After refluxing for 6 hours, the mixture was cooled and subjected to filtration to obtain a catalyst precursor F.

EXAMPLE 6

A catalyst precursor G was prepared in the same manner as in Example 1 except that the pH was adjusted to 1 with dilute hydrochloric acid at the time of adding the water/butanol solution.

EXAMPLE 7

A catalyst precursor H was prepared in the same manner as in Example 1 except that the pH was adjusted to 9 with dilute aqueous ammonia at the time of adding the water/butanol solution.

EXAMPLE 8

Figure 7:
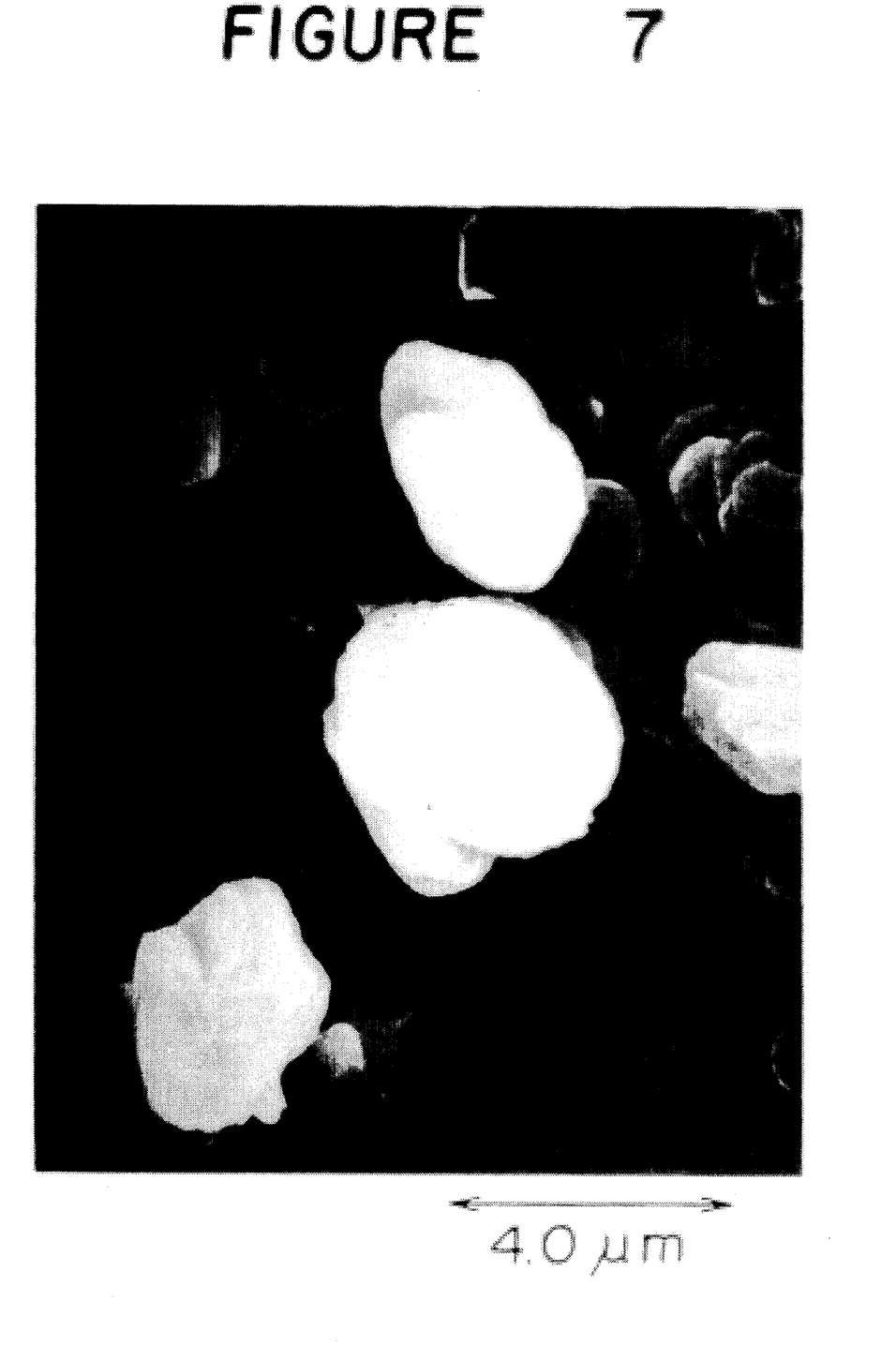
FIG. 7 is a photograph showing the particle structure of the catalyst precursor I obtained in Example 8 (6,000 magnifications).

150 ml of n-propanol was added as a solvent to 30 g of vanadium n-butoxide. Then, a n-propanol solution having 3.48 g of water dissolved therein, was slowly dropwise added thereto to hydrolyze the alkoxide. Then, 14.5 g of 85% phosphoric acid, 11.3 g of benzyl alcohol and 1.49 g of ferric chloride (hexahydrate) were added thereto, the temperature was raised with stirring, and refluxing was continued to obtain a blue solid. After refluxing for 6 hours, the mixture was cooled and subjected to filtration to obtain a catalyst precursor I. The catalyst precursor I had a size and shape as shown in FIG. 7.

REACTION EXAMPLE 1

Using the catalyst precursors obtained in Examples 1 and 8 and Comparative Example 1, gas phase catalytic oxidation of n-butane was carried out. Each catalyst precursor was calcined in a nitrogen atmosphere at about 600° C. and molded into tablets and then crashed into from 24 to 60 mesh, and the reaction was carried out under a condition of GHSV 10000 hr$^{-1}$. The analysis was conducted by gas chromatograph connected on line. The maximum yield of maleic anhydride and the optimum reaction temperature/optimum conversion giving the maximum yield, were obtained. The results are shown in Table 1.

TABLE 1

| Catalyst precursor | Average particle size (μm) | Optimum temp. (°C.) | Optimum conversion (%) | Maximum yield (%) |
| --- | --- | --- | --- | --- |
| A | 3.9 | 408 | 88.3 | 55.1 |
| B | 1.8 | 410 | 89.1 | 56.0 |
| C | 2.6 | 434 | 88.2 | 56.1 |
| D | 11.3 | 458 | 86.6 | 49.1 |
| E | 0.7 | 428 | 86.7 | 53.0 |
| F | 12.9 | 424 | 88.0 | 56.7 |
| G | 2.5 | 402 | 90.0 | 57.7 |
| H | 4.2 | 450 | 85.2 | 53.2 |
| I | 5.0 | 386 | 88.6 | 56.1 |

According to the process of the present invention, it is possible to design the shape of the catalyst capable of providing excellent catalytic activities and mechanical strength. Specifically, in the conventional processes for the preparation of the catalysts, after the production of a vanadium-phosphorus oxide catalyst precursor, it was necessary to adjust the particle size of such an oxide by a physical method such as pulverization at the time of pelletizing the oxide or at the time of forming a slurry for spray drying. Whereas, according to the process of the present invention, this pulverization step can be eliminated, and it is possible to simply obtain an industrial catalyst.

The catalyst obtainable from the vanadium-phosphorus oxide catalyst precursor produced by the present invention is useful for partial oxidation of a saturated and unsaturated hydrocarbon and a carboxylic acid, for example, for the production of maleic anhydride from a hydrocarbon having at least 4 carbon atoms such as n-butane, 1-butene, 2-butene, 1,3-butadiene or benzene, the production of acrylic acid or acrolein from propane, or the production of methacrylic acid from isobutyric acid.

What is claimed is:

1. A process for producing a vanadium-phosphorus oxide-containing catalyst precursor in the liquid phase and in the absence of a support, which comprises (a) introducing into an organic solvent a vanadium alkoxide as a pentavalent vanadium compound and a phosphorus compound in the presence of a reducing agent capable of reducing the pentavalent vanadium compound to a tetravalent state, (b) hydrolyzing at least a part of the vanadium alkoxide before or after the introduction of the phosphorus compound, and (c) heating the vanadium-containing liquid medium obtained in step (b), in the presence of the phosphorus compound to reduce at least a part of vanadium to a tetravalent state.

2. The process according to claim 1, wherein the vanadium alkoxide introduced into the organic solvent is the one prepared by converting at least 50% of a pentavalent vanadium compound to a vanadium alkoxide.

3. The process according to claim 1, wherein the vanadium alkoxide is a dehydrative condensation product of a $C_{1-5}$ alcohol with vanadium pentoxide.

4. The process according to claim 1, wherein the vanadium alkoxide is vanadium methoxide.

5. The process according to claim 1, wherein the vanadium alkoxide is vanadium ethoxide.

6. The process according to claim 1, wherein the vanadium alkoxide is vanadium propoxide.

7. The process according to claim 1, wherein the vanadium alkoxide is vanadium butoxide.

8. The process according to claim 1, wherein the phosphorus compound is orthophosphoric acid.

9. The process according to claim 1, wherein the proportions of vanadium alkoxide and the phosphorus compound are such that the atomic ratio of phosphorus/vanadium is from 1.0 to 1.5.

10. The process according to claim 1, wherein the organic solvent is a reducing organic compound.

11. The process according to claim 1, wherein the organic solvent is an alcohol.

12. The process according to claim 1, wherein the organic solvent is a $C_{3-6}$ aliphatic alcohol.

13. The process according to claim 1, wherein the reducing agent is benzyl alcohol.

14. The process according to claim 1, wherein the organic solvent is a mixture of a $C_{3-6}$ aliphatic alcohol and benzyl alcohol.

15. The process according to claim 1, wherein the amount of the organic solvent is from 1 to 30 parts by weight per part by weight of the total amount of the vanadium alkoxide and the phosphorus compound.

16. The process according to claim 1, wherein at least a part of the vanadium alkoxide is hydrolyzed, followed by reaction with the phosphorus compound.

17. The process according to claim 16, wherein water is added to the organic solvent solution of the vanadium alkoxide.

18. The process according to claim 16, wherein the hydrolysis of the vanadium alkoxide is conducted at a temperature of from 0° to 150° C.

19. The process according to claim 16, wherein the amount of water added for the hydrolysis of the vanadium alkoxide is from 0.5 to 20 mols per mol of the vanadium alkoxide.

20. The process according to claim 16, wherein the hydrolysis of the vanadium alkoxide is conducted in the presence of an acid.

21. The process according to claim 16, wherein the hydrolysis of the vanadium alkoxide is conducted in the presence of a base.

22. The process according to claim 16, wherein the hydrolysis of the vanadium alkoxide is conducted at a pH within a range of from 0 to 12.

23. The process according to claim 16, wherein the hydrolysis of the vanadium alkoxide is followed by aging from 0.1 to 10 hours.

24. The process according to claim 16, wherein the reaction with the phosphorus compound is conducted under heating and refluxing.

25. The process according to claim 16, wherein the hydrolysis of the vanadium alkoxide is followed by heating and refluxing, then the phosphorus compound is added thereto, and the mixture is again heated and refluxed.

26. The process according to claim 25, wherein the heating and refluxing are conducted for from 0.5 to 20 hours.

27. The process according to claim 1, wherein into the organic solvent, the vanadium alkoxide as a pentavalent vanadium compound and the phosphorus compound are introduced in the presence of the reducing agent capable of reducing the pentavalent vanadium compound to a tetravalent state, and then a part of the vanadium alkoxide is hydrolyzed.

28. The process according to claim 27, wherein the vanadium alkoxide is added to an organic solvent solution containing the phosphorus compound.

29. The process according to claim 27, wherein the vanadium alkoxide is added to an organic solvent solution containing the phosphorus compound, followed by heating and refluxing.

30. The process according to claim 29, wherein the heating and refluxing are conducted for from 0.5 to 20 hours.

31. The process according to claim 29, wherein water is added within a period of from 0 to 2 hours from the initiation of the heating and refluxing.

32. The process according to claim 27, wherein the amount of water added for the hydrolysis of the vanadium alkoxide is from 0.5 to 20 mols per mol of the vanadium alkoxide.

33. The process according to claim 1, wherein the catalyst precursor contains, as a co-catalyst metal component, at least one member selected from the group consisting of chromium, iron, nickel, cobalt, zinc, ruthenium, and zirconium.

34. The process according to claim 33, wherein the amount of the co-catalyst metal component is from 0.001 to 0.30 mol per mol of vanadium.

\* \* \* \* \*